United States Patent
Buchegger

(10) Patent No.: US 8,951,042 B2
(45) Date of Patent: Feb. 10, 2015

(54) DENTAL PROSTHESIS

(75) Inventor: Harald Buchegger, St. Konrad (AT)

(73) Assignees: Redtenbacher Praezisionsteile Ges.m.b.H., Scharnstein (AT); Gerwin Vincent Arnetzl, Graz (AT)

( * ) Notice: Subject to any disclaimer, the term of this patent is extended or adjusted under 35 U.S.C. 154(b) by 0 days.

(21) Appl. No.: 14/112,130

(22) PCT Filed: Apr. 5, 2012

(86) PCT No.: PCT/AT2012/050045
§ 371 (c)(1),
(2), (4) Date: Oct. 16, 2013

(87) PCT Pub. No.: WO2012/142640
PCT Pub. Date: Oct. 26, 2012

(65) Prior Publication Data
US 2014/0045145 A1    Feb. 13, 2014

(30) Foreign Application Priority Data
Apr. 20, 2011 (AT) ...................................... 560/2011

(51) Int. Cl.
*A61C 8/00* (2006.01)
(52) U.S. Cl.
CPC ............. *A61C 8/0069* (2013.01); *A61C 8/0068* (2013.01); *A61C 8/0072* (2013.01); *A61C 8/0037* (2013.01)
USPC .......................................... 433/173; 433/174
(58) Field of Classification Search
USPC .................................................. 433/173, 174
See application file for complete search history.

(56) References Cited

U.S. PATENT DOCUMENTS

| 4,932,868 | A  |   | 6/1990  | Linkow et al. |
|-----------|----|---|---------|---------------|
| 5,022,860 | A  | * | 6/1991  | Lazzara et al. ................ 433/174 |
| 5,829,977 | A  | * | 11/1998 | Rogers et al. ................. 433/172 |
| 6,474,991 | B1 | * | 11/2002 | Hansson ....................... 433/173 |
| 6,824,386 | B2 | * | 11/2004 | Halldin et al. ................ 433/173 |
| 7,175,434 | B2 | * | 2/2007  | Brajnovic ..................... 433/174 |

(Continued)

FOREIGN PATENT DOCUMENTS

DE        10340059 A1   2/2005
DE    202006013585 U1  11/2006

(Continued)

OTHER PUBLICATIONS

International Search Report of PCT/AT2012/050045, mailed Aug. 2, 2012.

Primary Examiner — Ralph Lewis
(74) Attorney, Agent, or Firm — Collard & Roe, P.C.

(57) ABSTRACT

The invention relates to a dental prosthesis, comprising an implant body (1) and an abutment (2) that can be inserted into a receptacle of the implant body (1), said abutment (2) forming a passage opening (4) for accommodating a cap screw (3) that engages in an internal thread (5) of the implant body (1), which screw is supported by means of a conical cap part (7) of the cap screw (3) on a conical shoulder (8) of the abutment (2). In order to provide advantageous constructional conditions it is proposed that the conical cap part (7) has at least two consecutive conical sections (9, 10) in the axial direction, which conical sections have an opening angle that differs from the opening angle of the conical shoulder (8), and when the one conical section (9) contacts the conical shoulder (8) without pressure the other conical section (10) engages in the shoulder cone (11) with play.

5 Claims, 2 Drawing Sheets

(56) References Cited

U.S. PATENT DOCUMENTS

2003/0235802 A1* 12/2003 Martina .................. 433/174
2005/0287497 A1   12/2005 Carter
2008/0057477 A1    3/2008 Rosen
2011/0008753 A1    1/2011 Rupprecht et al.
2013/0108986 A1*  5/2013 Lee ....................... 433/174

FOREIGN PATENT DOCUMENTS

| EP | 1374796 A1 | 1/2004 |
| WO | 00/62704 A1 | 10/2000 |
| WO | 2009/106205 A1 | 9/2009 |

\* cited by examiner

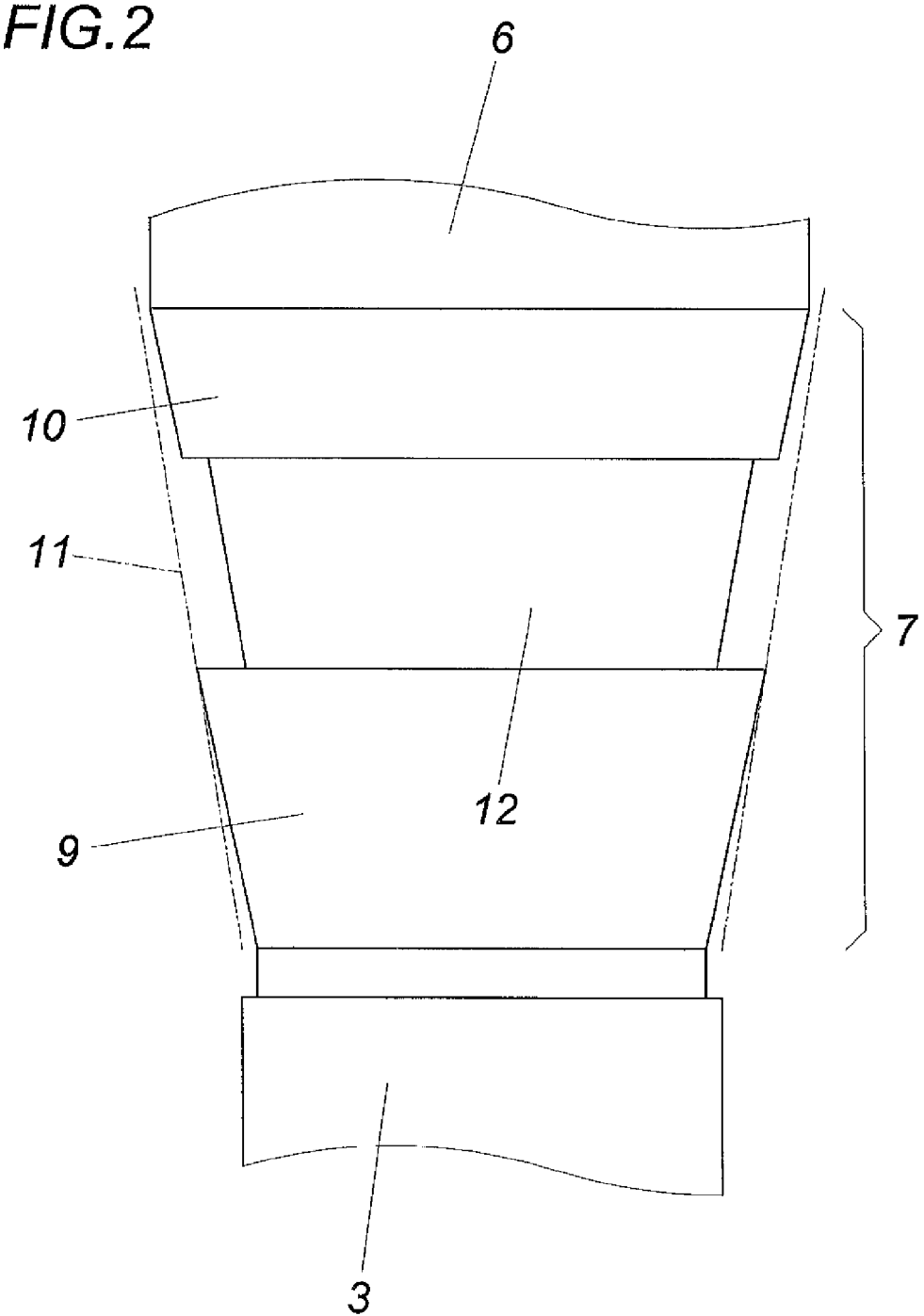

DENTAL PROSTHESIS

CROSS REFERENCE TO RELATED APPLICATIONS

This application is the National Stage of PCT/AT2012/050045 filed on Apr. 5, 2012, which claims priority under 35 U.S.C. §119 of Austrian Application No. A 560/2011 filed on Apr. 20, 2011, the disclosure of which is incorporated by reference. The international application under PCT article 21(2) was not published in English.

1. FIELD OF THE INVENTION

The invention relates to a dental prosthesis, comprising an implant body and an abutment that can be inserted into a receptacle of the implant body, said abutment forming a passage opening for accommodating a cap screw that engages in an internal thread of the implant body, which screw is supported by means of a conical cap part on a conical shoulder of the abutment.

2. DESCRIPTION OF THE PRIOR ART

Dental prostheses are usually arranged in such a way that an implant body inserted into the jawbone accommodates an abutment for building the dental prosthesis. This abutment is connected by means of a cap screw to the implant body which is inserted into a passage opening of the abutment and engages into an internal thread of the implant body. The screw cap rests on an annular shoulder of the abutment, wherein it is demanded that the cap screw is unable to loosen inadvertently and enables a tight connection to the abutment, so that no bacteria can reach the implant body. In order to meet these requirements, it is known (DE 103 40 059 A1, DE 20 2006 013 585 U1) to provide the screw cap with a conical cap part which rests on a conical annular shoulder. Although this conical arrangement of the support surfaces leads to an improvement concerning the support of the screw cap in relation to the abutment, these known screw connections can fulfil the demands placed thereon only to a certain extent.

In order to ensure a screw connection in hinges of a spectacle frame which is secured against loosening, it is further known to arrange the cone angle of a conical screw cap in relation to the conical receptacle of the screw cap in a different way, so that high friction is obtained between the conical surfaces and therefore the likelihood of self-loosening is reduced. The requirements placed on screw connections of spectacle hinges cannot be compared to the requirements placed on the screw connections between the abutment and implant body however since the problem of tightness is irrelevant in screw connections for spectacle hinges.

SUMMARY OF THE INVENTION

The invention is therefore based on the object of providing a dental prosthesis of the kind mentioned above in such a way that the tightness of the connection between the abutment and the implant body is ensured and self-loosening of the screw connection can be excluded.

This object is achieved by the invention in such a way that the conical cap part of the cap screw has at least two consecutive conical sections in the axial direction, which conical sections have an opening angle that differs from the opening angle of the conical shoulder, and when the one conical section contacts the conical shoulder without pressure the other conical section engages in the shoulder cone with play.

By providing at least two conical sections which are consecutive in the axial direction and which have different diameters with respect to the conical shoulder, it occurs as a result of the different opening angles of the cones of the shoulder on the one hand and the conical sections of the screw cap on the other hand when the cap screw is tightened that at first the one conical section of the cap screw is pressed against the conical shoulder of the abutment under elastic and plastic deformation of the conical shoulder of the abutment and the respective conical section of the cap screw before the other conical section comes to rest thereon and subsequently forms an additional sealing surface at least under elastic deformation of the cooperating conical surfaces. The required tightness of the screw connection can thus be ensured by the resulting, at least two-stage sealing of the screw cap in relation to the abutment. Furthermore, the frictional resistance is increased by the plastic and elastic deformation of the cooperating conical surfaces in such a way that the likelihood of self-loosening of the screw connection can be excluded.

Especially simple constructional conditions are obtained when the two conical sections of the cap screw have the same cone angle, which is not mandatory however. If the cone angles of the cap screw are larger than the cone angle of the conical shoulder, the sealing surfaces are advantageously obtained in the region of the largest diameter of the two cone sections of the conical cap part.

For the production of the two cone sections it is recommended to provide these cone sections at an axial distance from each other. Furthermore, advantageous conditions are further obtained concerning the sealing areas when the cap screw is tightened in that the conical section engaging with play in the shoulder cone during contact of the one conical section on the conical shoulder has a shorter axial length because when the cap screw is tightened the engagement length of said conical section of the cap screw engaging initially with play in the shoulder cone is respectively shorter.

BRIEF DESCRIPTION OF THE DRAWINGS

The subject matter of the invention is shown by way of example in the drawings, wherein:

FIG. 2 shows the conical cap part of cap screw in an enlarged side view.

DESCRIPTION OF THE PREFERRED EMBODIMENT

Figure 1:
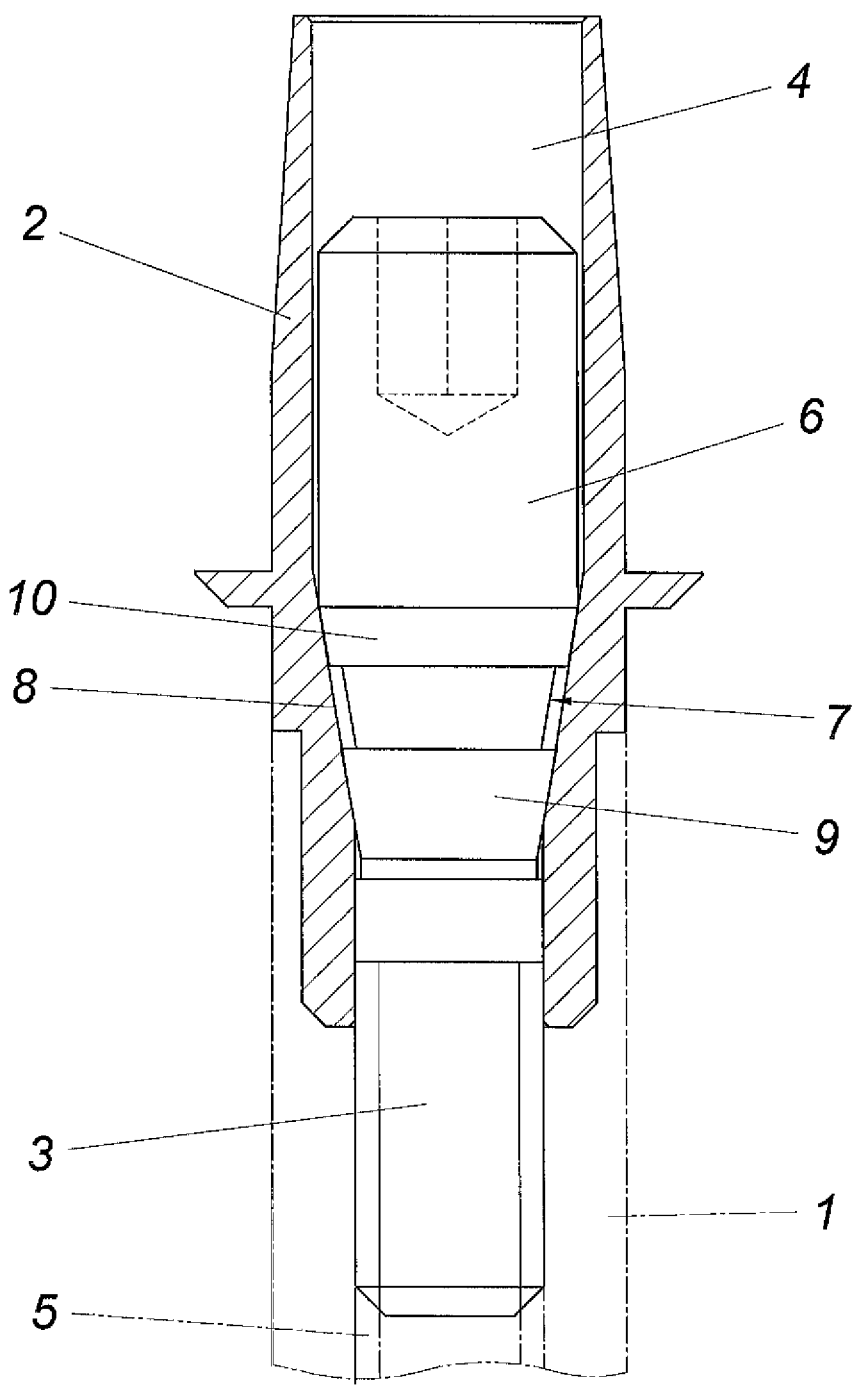
FIG. 1 shows a dental prosthesis in accordance with the invention in a schematic longitudinal sectional view.

The dental prosthesis according to FIG. 1 comprises in the conventional manner an implant body 1 to be inserted into the jawbone and indicated by the dot-dash line for accommodating an abutment 2 for a dental prosthesis. Said abutment 2 is connected by means of a cap screw 3 to the implant body 1. For this purpose, the abutment 2 is provided with a passage opening 4, into which the cap screw 3 is inserted which engages in an internal thread 5. The screw cap 6 comprises a conical cap part 7 which cooperates with a conical shoulder 8 of the abutment 4 and presses the abutment 2 into its receptacle in the implant body 1 via said conical shoulder 8.

As is shown especially in FIG. 2, the conical cap part 7 comprises two consecutive conical sections 9 and 10 in the axial direction. Although said conical sections 9 and 10 have a corresponding cone angle, the cone tips are disposed at an axial distance from each other on the screw axis, so that the one conical section 9 already strikes the shoulder cone 11 of the conical shoulder 8 of the abutment 2 which is indicated by the dot-dash line, whereas the other conical section 10 still has play in relation to the shoulder cone 11. Since the cone angle of the conical sections 9, 10 have been chosen differently with respect to the cone angle of the shoulder cone 11 (the cone angle of the conical sections 9, 10 is preferably chosen larger than the cone angle of the shoulder cone 11), the conical section 9 will press at first into the conical shoulder 8 in the region of the largest diameter when the cap screw 3 is tightened under deformation of the conical shoulder 8 and the conical section 9 which extends into the plastic region before conical section 10 takes effect and forms a second sealing surface under an at least elastic deformation of the conical surfaces.

By an adjusting the cone angles with respect to each other and to the respective material properties, advantageous conditions for the screw connection can be obtained between the abutment 2 and the implant body 1. Conventional cone angles lie in a range of between 10 and 30°, wherein the difference in the cone angles can lie in the range of 1 to 5° for the conical shoulder 8 on the one hand and the conical cap part 7 on the other hand. The play between the conical section 10 and the shoulder cone 11 in pressureless contact of the conical section 9 on the shoulder cone 11 should generally not exceed 0.1 mm. These values are not limiting and can be exceeded or fall short of if required. As is shown in the embodiment, the conical sections 9 and 10 are arranged at an axial distance from each other, wherein a re-entrant cap section 12 is obtained between these sections 9 and 10 which facilitates the production of the conical sections 9 and 10. In the illustrated embodiment, the cone angles of the two conical sections 9 and 10 are chosen equally large for constructional reasons. This is in no way mandatory however. On the contrary, the sealing effect and the self-locking configuration of the screw connection may be improved with different cone angles under certain circumstances.

The invention claimed is:

1. A dental prosthesis comprising:
   a cap screw having a screw head and a conical cap part disposed axially behind said screw head,
   an implant body having a receptacle and an internal thread disposed axially in front of the receptacle, and
   an abutment inserted into the receptacle of the implant body and forming a passage opening for accommodating the cap screw, said passage opening comprising a first opening region and a conical shoulder disposed axially adjacent said first opening region, said conical shoulder having an opening angle,
   wherein when the cap screw is inserted into the passage opening of the abutment, the screw head of the cap screw engages in the internal thread of the implant body,
   wherein the cap screw is supported via the conical cap part on the conical shoulder of the abutment,
   wherein the conical cap part has at least a first conical section and a second conical section disposed consecutively in an axial direction, the first and second conical sections having respective conical angles that differ from the opening angle of the conical shoulder, and
   wherein when the first conical section contacts the conical shoulder without pressure the second conical section engages with play into the conical shoulder and when the second conical section contacts the conical shoulder without pressure the first conical section engages with play into the conical shoulder.

2. The dental prosthesis according to claim 1, wherein the first and second conical sections of the cap screw have the same conical angle.

3. The dental prosthesis according to claim 1, wherein the conical angles of the cap screw are larger than the opening angle of the conical shoulder of the abutment.

4. The dental prosthesis according to claim 1, wherein the first and second conical sections follow one another at an axial distance.

5. The dental prosthesis according to claim 1, wherein the second conical section has an axial length shorter than an axial length of the first conical section.

\* \* \* \* \*